(12) United States Patent
Rabenstein et al.

(10) Patent No.: US 6,686,443 B1
(45) Date of Patent: Feb. 3, 2004

(54) CHEMICAL REAGENTS FOR FORMATION OF DISULFIDE BONDS IN PEPTIDES

(75) Inventors: Dallas L. Rabenstein, Riverside, CA (US); Tiesheng Shi, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/579,883

(22) Filed: May 26, 2000

(51) Int. Cl.⁷ .................................................. A61K 38/00

(52) U.S. Cl. ...................... 530/320; 530/300; 530/333; 530/345; 514/2

(58) Field of Search ................................. 530/300, 304, 530/333, 345, 402, 408; 514/2

(56) References Cited

PUBLICATIONS

Andreu et al. (1994) "Formation of Disulfide Bonds in Synthetic Peptides and Proteins," Pp. 91–169 In *Peptide Synthesis Protocols;* Pennington, M.W., Bunn, B.M., Ed.; Humana Press: New Jersey.
Annis and Barany (1997) "Disulfide Bond Formation in Peptides" *Meth. Enzymol.,* 289:198–221.
Annis and Barany (1998) "Novel Solid–Phase Reagents for Facilie Formation of Intramolecular Disulfide Bridges in Peptides under Mild Conditions." *J. Am. Chem. Soc.,* 120:7226–7238.
Bankowski and Manning (1978) "Design of Potent Antagonists of the Vasopressor to Arginine–vasopressin." *Med. Chem.* 21:850–853.
Bard et al. (1985) "Platinum" pp. 345–365 In: *Standard Potentials in Aqueous Solution,* Marcel Dekker: N.Y.
Basolo et al. (1950) "The Stereochemistry of Complex Inorganic compounds X. The Stereoisomers of Dichloris-(ethylenediamine)–platinum (IV) Chloride," *J. Am. Chem. Soc.* 72:2433–2438.
Frohling and Sheldrick (1997) "Intramolecular competition between histidine and methionine side chains in reactions of dipeptides with [Pt(en)(H$_2$O$_2$)]$^{2+}$ (en=H$_2$NCH$_2$CH$_2$NH$_2$)" *J. Chem. Soc. Dalton Trans.,* 4411–4420.
Fujii et al. (1987) "Studies on Peptides. CLI. Synthesis if Cystine–Peptides by Oxidation of S–Protected Cysteine–Peptides with Thallium (III) Trifluoroacetate." *Chem. Pharm. Bull.,* 35:2339–2347.
Goldberg amd Helper (1968) "Thermochemistry and Oxidation Potentials of the Platinum Group Metals and Their Compounds." *Chem. Rev.* 68:229–252.
Hope et al. (1962) "A Highly Potent Analogue of Oxytocin, Desamino–oxytocin." *J. Biol. Chem.* 237: 1563–1566.
Hruby et al. (1977) "Comparative Use of Benzhydrylamine and Chloromethylated Resins in Solid–Phase Synthesis of Carboxamide Terminal Peptides. Synthesis of Oxytocin Derivatives." *J. Org. Chem.* 42:3552–3556.

Larive and Rabenstein (1993) Dynamics of Cis/Trans Isomerization of the Cysteine–Proline Peptide Bonds of Oxytocin and Arginine–Vasopressin in Aqueous and Methanol Solutions. *J. Am. Chem. Soc.,* 115:2833–2836.
Lavielle et al. (1988) "Analysis of Tachykinin Binding site Interactions using contrained Analogues of Tachykinins." *J. Biochem. Pharmacol.* 37:41–49.
Lazure et al. (1988) "The amino acid sequences of frog heart atrial natriuretic–like peptides and mammalian ANF are closely related." *FEBS Letters,* 238:300–306.
Live et al. (1977) "A Rapid, Efficient Synthesis of Oxytocin and 8–Arginine–vasopressin. Comparison of Benzyl, p–Methoxybenzyl, and p–Methylbenzyl as Protecting Groups for Cysteine." *J. Org. Chem.* 42:3566–3561.
Moore et al. (1978) "Influence of the Peptide–Chain Length on Disulphide–Bond Formation in Neurohypophysial Hormones and Analogues." *Biochem. J.* 173:403–409.
Moroder et al. (1996) "Oxidative Folding of Cystine–Rich Peptides vs Regioselective Cysteine Pairing Strategies." *Biopolymers* 40:207–234.
Munson and Barany (1993) "Synthesis of α–Conotoxin SI, a Bicyclic Tridecapeptide Amide with Two Disulfide Bridges: Illustration of Novel Protection Schemes and Oxidation Strategies." *J. Am. Chem. Soc.* 115: 10203–10216.
Noszal et al. (1992) "Characterization of the Macroscopic and Microscopic Acid–Base Chemistry of the Native Disulfide and Reduced Dithiol Forms of Oxytocin, Arginine–Vasopressin and Related Peptides," *J. Org. Chem.* 57:2327–2334.
Poë (1963) "The Relative Satilities of Halogeno–complexes. Part III. The trans–Pt en$_2$Cl$_2$$^{2+}$—Br$^-$ Equilibria." *J. Chem. Soc.* 183–188.
Rabenstein and Weaver (1996) "Kinetics and Equilibria of the Thio/Disulfide Exchange Reactions of Somatostatin with Glutathione." *J. Org. Chem.* 61:7391–7397.
Rabenstein and Yeo (1994) "Kinetics and Equilibria of the Formation and Reduction of the Dislufide Bonds in Arginine–Vasopressin and Oxytocin by Thiol/Disulfide Interchange with Glutathione and Cysteine." *J. Org. Chem.* 59:4223–4229.
Shi and Elding (1998) "Kinetics and Mechanism for reduction of trans–dichlorotetracyanoplatinate (IV) by tetraammineplatinum (II) and bis (ethylenediamine) platinum (II)." *J. Inorg. Chim. Acta.* 282:55–60.

(List continued on next page.)

*Primary Examiner*—Brenda Brumback
*Assistant Examiner*—Roy Teller
(74) *Attorney, Agent, or Firm*—Quine Intellectual Property Law Group, PC; Tom Hunter

(57) ABSTRACT

This invention pertains to the discovery of a class of reagents that effectively form intramolecular disulfide bonds in peptides. Intermolecular disulfide linkage formation is low or essentially non-existent. In addition, preferred reagents of this invention are relatively mild and do not oxidize "vulnerable" residues in the subject peptide(s). In addition the reagents and reaction products are safe and essentially non-toxic. One particularly preferred reagent is [Pt(en)$_2$Cl$_2$] 2+ where en is ethylenediamine.

46 Claims, 7 Drawing Sheets-

OTHER PUBLICATIONS

Shi and Rabenstein (1999) "trans–Dichlorotetracyanoplatinate (IV) as a Reagent for the Rapid and Quantitative Formation of Intramolecular Disulfide Bonds in Peptides." *J. Org. Chem.* 64:4590–4595.

Shi and Rabenstein (2000) "Discovery of a Highly Selective and Efficient Reagent for Formation of Intramolecular Disulfide Bonds in Peptides," J. Am. Chem. Soc., 122(29):5075–5089.

Shit et al. (1996) "Kinetics and Mechanism for Reduction of trans–Dichlorotetracyanoplatinate (IV) by Thioglycolic Acid, L–Cysteine, DL–Penicillamine, and Glutathione in Aqueous Solution." *Inorg. Chem.* 35:3498–3502.

Shi et al. (1997) "Reduction of trans–dichloro–and transdibromo–tetracyanoplatinate (IV) by L–methionine." *J. Chem. Soc., Dalton Trans.* 2073–2077.

Shik (1993) "New Approaches to the Synthesis of Cystine Peptides Using N–iodosuccinimide in the Construction of Disulfide Bridges." *J. Org. Chem.* 58:3003–3008.

Tam et al. (1991) "Disulfide Bond Formation in Peptides by Dimethyl Sulfoxide, Scope and Applications." *J. Am. Chem. Soc.* 11 (might be vol. 111); 6657–6662.

Wilmarth et al. (1983) "Kinetics and Mechanisms of the Reduction of trans–Tetrcyanohydroxobromoplatinate(IV) and its pronated form by some inorganic anions." *Coord. Chem. Rev.* 51:141–153.

International PCT Search Report.

Frohling et al. (1997) "Intramolecular Competition Between Histidine and Methionine Side Chains in Reactions of Dipeptides with [Pt(en)(H2O2]2+(en=H2NCH2CH2NH2)" J. Chem. Soc. Dalton Trans., pp 4411–4420.

Shi et al. (2000) "Discovery of a Highly Selective and Efifcient Reagent for Formation of Intramolecular Disulfide Bonds in Peptides", J. Am. Chem. Soc. 122(29):6809–6815.

Scheme 1

CHEMICAL REAGENTS FOR FORMATION OF DISULFIDE BONDS IN PEPTIDES

STATEMENT AS TO RIGHTS TO INVENTIONS MADE UNDER FEDERALLY SPONSORED RESEARCH AND DEVELOPMENT

This invention was made with Government support under Grant No: GM37000, awarded by the National Institutes of Health. The Government of the United States of America may have certain rights in this invention.

CROSS-REFERENCE TO RELATED APPLICATIONS

[Not Applicable]

FIELD OF THE INVENTION

This invention pertains to the field of peptide chemistry. In particular, this invention provides reagents that effectively form intramolecular disulfide bonds in peptides bearing sulfhydryl groups.

BACKGROUND OF THE INVENTION

The chemical assembly of suitably derivatized amino acids to produce chemically synthesized peptides has become a well developed art. Indeed, a number of machines for the chemical synthesis of peptides are commercially available (see, e.g., *PerSeptive Biosystems, Applied Biosystems*, Advanced ChemTech Venture, etc.). Such chemical syntheses proceed by the stepwise addition of amino acid residues to produce a linear peptide. Frequently, however, it is desirable to introduce or alter secondary structure by the formation of intramolecular linkages in a particular peptide. Such intramolecular linkages typically take the form of disulfide linkages, most typically formed between two cysteines that have sulfhydryl (SH) groups available for reaction.

Although formation of intrapeptide disulfide bonds can often be achieved by oxidation of the free thiol or sulfur-protected precursors under varying reaction conditions, a continuing challenge in peptide synthesis has been to develop more efficient and selective methods (Andreu et al. (1994) Pages 91–169 In *Peptide Synthesis Protocols*; Pennington, M. W., Bunn, B. M., Ed.; Humana Press: New Jersey; Moroder et al. (1996) *Biopolymers* 40: 207–234; Annis and Barany (1997) *Meth. Enzymol.*, 289: 198–221; Tam et al. (1991) *J. Am. Chem. Soc.* 111:, 6657–6662; Munson and Barany (1993) *J. Am. Chem. Soc.* 115: 10203–10216; Shik (1993) *J. Org. Chem.* 58: 3003–3008; Annis and Barany (1998) *J. Am. Chem. Soc.*, 120: 7226–7238; Shi and Rabenstein (1999) *J. Org. Chem.* 64: 4590–4595). A variety of oxidants have been explored for formation of disulfide bonds, however, all have drawbacks and some limitations in practical use, including formation of dimers/oligomers and/or side reactions on the side chains of methionine, tyrosine and Tryptophan (Id.). For instance, thallium(III) trifluroacetate is a mild oxidant that can be employed as an alternative to iodine, and it gives a higher efficiency in some cases (Fujii et al. (1987) *Chem. Pharm. Bull.*, 35: 2339–2347). The major drawback of this reagent is its high toxicity, and moreover, thallium can be difficult to remove from sulfur-containing peptides due to its high affinity to sulfur.

SUMMARY OF THE INVENTION

This invention pertains to the discovery of a class of reagents that effectively form intramolecular disulfide bonds in peptides. Intermolecular disulfide linkage formation is low or essentially non-existent. In addition, preferred reagents of this invention are relatively mild and do not oxidize "vulnerable" residues in the subject peptide(s). In addition the reagents and reaction products are safe and essentially non-toxic.

Thus, in one embodiment, this invention provides methods of forming an intramolecular disulfide bond in a peptide. The methods preferably involve contacting a peptide comprising at least two sulfhydryl (SH) groups with disulfide-linkage-forming reagent as described herein (see, e.g., Formula I and species thereof). In preferred embodiments, the reagent concentration is sufficient to produce one or more intramolecular disulfide linkages in the subject peptide(s). Particularly preferred reagents used in this context include, but are not limited to trans-$[Pt(CN)_4Cl_2]^{2-}$, and trans-$[Pt(en)_2Cl_2]^{2+}$ (en=ethylenediamine), although trans-$[Pt(CN)_4Cl_2]^{2-}$ is most preferably used with peptides lacking a methionine. Preferred peptides for use in these methods range in length from about 2 to 200 amino acids, preferably from about 2 to about 100 amino acids, more preferably from about 2 to about 80 amino acids, and most preferably from about 2 to about 50 amino acids. The amino acids that form the disulfide linkage can be adjacent to each other or at essentially any distance away from each other on the peptide backbone so long as they can be juxtaposed sufficiently close (e.g. by peptide folding) to form a disulfide linkage. In certain preferred embodiments, the two amino acids that form a disulfide bond are separated by no more than about 58 amino acids. In certain preferred embodiments, the peptide contains a methionine. The contacting is preferably at a pH ranging from about pH 0 or pH 1 to about pH 9. The peptide can be a chemically synthesized peptide, a recombinantly expressed peptide, a cleavage product of a larger protein or peptide, a peptide isolated from a biological sample (e.g. a tissue, cell, organ, bioreactor, etc.). The peptide may bear a protecting group (e.g. an Fmoc or a tBoc).

In another embodiment, this invention comprises a solution comprising a peptide comprising at least two sulfur groups; and a disulfide linkage forming reagent as described herein (see, e.g., formula I and associated species). Such a solution is useful as a positive control when evaluating the efficacy of particular reagent species. In addition, such a solution is useful as a sample solution when optimizing a purification protocol to "clean up" or isolate the desired reaction product (e.g. when optimizing an HPLC protocol or evaluating a particular chromatography column). In preferred embodiments, the peptide in the solution is a peptide as described above. The peptide can be in solution or attached to a solid support (e.g. a peptide synthesis resin). The solution is preferably a buffered solution (e.g. at a pH ranging from pH 0 or pH 1 to about pH 9).

This invention also provides a peptide synthesizer for the synthesis of a peptide having an intramolecular disulfide linkage. A preferred synthesizer comprises a plurality of vials, said vials containing amino acids derivatized for chemical peptide synthesis wherein at least one of said vials comprises an amino acid that, when fully deprotected, bears a sulfhydryl (SH) group; and a vial comprising a disulfide linkage-forming reagent as described herein (see, e.g., Formula I and associated species described herein).

In still another embodiment this invention provides a method of chemically synthesizing a peptide comprising a disulfide linkage. The method involves chemically coupling a plurality of amino acids to form a peptide comprising at least two sulfhydryl (SH) groups; and contacting the peptide with a disulfide linkage-forming reagent (e.g. Formula I and associated species) as described herein.

This invention also provides a kit for forming an intramolecular disulfide bond in a peptide. The kit preferably comprises a container containing a disulfide linkage forming reagent (Formula I and associated species as described herein) instructional materials teaching the use of the reagent to form disulfide linkages in a peptide. In certain embodiments, the reagent is provided as a dry powder, while in other embodiments the reagent is in a buffer at a pH ranging from about pH 1 to about pH 9.

In certain preferred embodiments the methods, compositions, and generic formulas of this invention expressly exclude $[Pt(CN)_4Cl_2]^{2-}$. In certain preferred embodiments the methods, compositions, and generic formulas of this invention expressly exclude $[Pt(CN)_4X^2]^{2-}$ where X is Cl—, Br—, I—, or RCOO— (where R is alkyl). Definitions.

The term peptide refers to a polymer of amino acid residues. Preferred peptides range in length from about 2 to about 100 amino acids. The term also applies to linear or branched amino acid polymers in which one or more amino acid residues is an artificial chemical analogue of a corresponding naturally occurring amino acid, as well as to naturally occurring amino acid polymers. The term also includes variants on the traditional peptide linkage joining the amino acids making up the polypeptide.

The term "alkyl" refers to a paraffinic hydrocarbon group which may be derived from an alkane by dropping one hydrogen from the formula. Examples are methyl ($CH_3$—), ethyl ($C_2H_5$—), propyl ($CH_3CH_2CH_2$—), isopropyl (($CH_3)_2CH_3$—).

The term "substituted alkyl" refers to a group which may be derived from a paraffinic hydrocarbon group by substitution, e.g. of a hydroxyl group for a hydrogen. Examples are $HOCH_2CH_2$—, $CH_3CH(OH)CH_2$—, and the like.

The term "aromatic" refers to an organic molecule that contains a benzene ring or a benzene-derived ring. Examples of aromatic linkers include, but are not limited to —$C_6H_4$—, —$CH_2C_6H_4$— and —$CH_2C_6H_4CH_2$—.

A "nitrogen, oxygen, phosphorus or sulfur ligand" refers to a nitrogen, oxygen, phosphorus, or sulfer typically attached to the Pt (Pt(IV)) and bearing appropriate substituents. Thus, for example, a nitrogen ligand includes, but is not limited to, cyanide, ammonia, amine nitrogen, and the like. An oxygen ligand includes, but is not limited to, a carboxylate oxygen, and the like. A phosphorous ligand includes, but is not limited to a phosphine phosphorous, a thioether sulfer, and the like.

DETAILED DESCRIPTION

Figure 1:
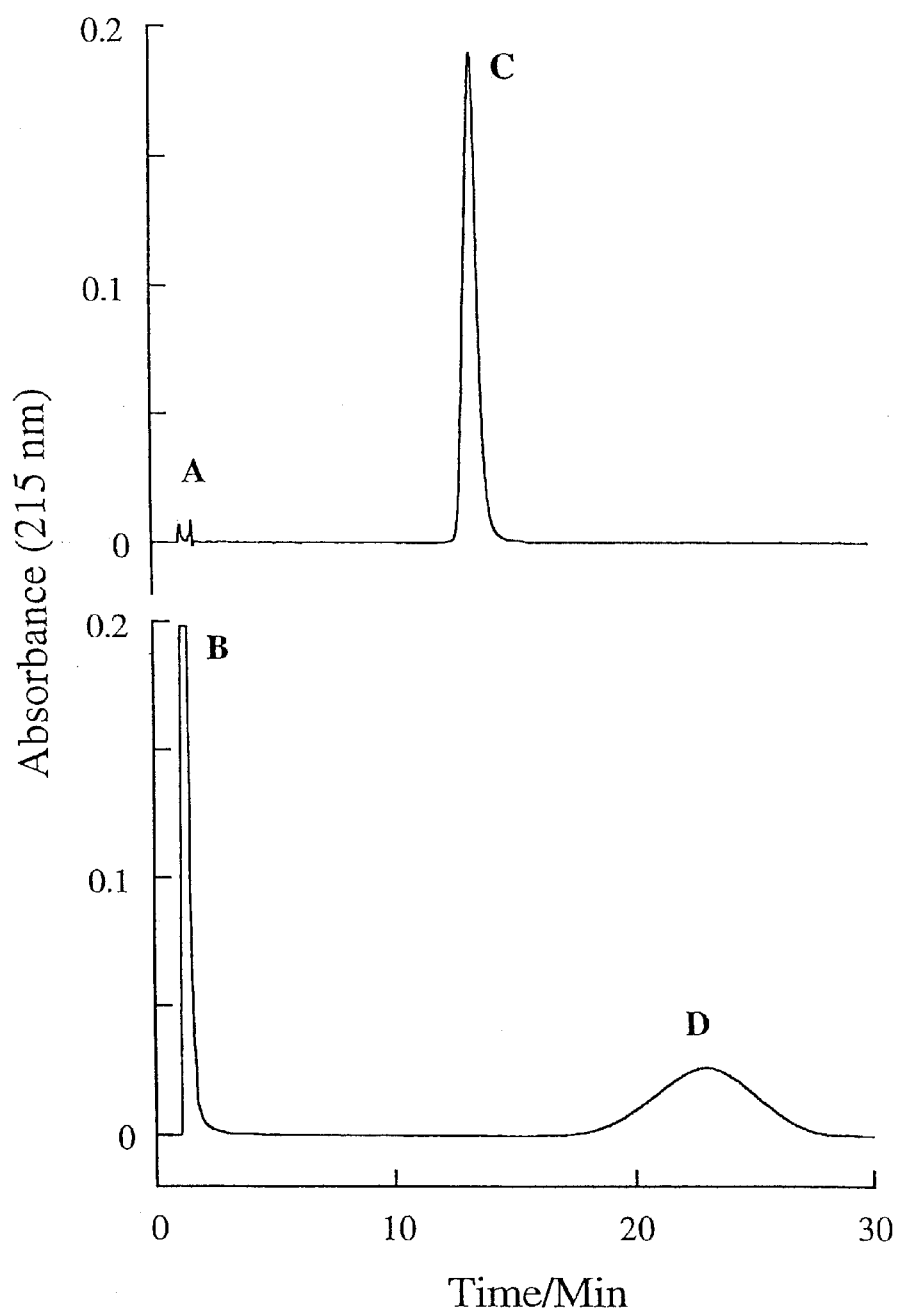
FIG. 1 shows chromatograms of 80 $\mu$M 1 in water (top) and the products from the reaction of 80 $\mu$M 1 and 150 $\mu$M $[Pt(en)_2Cl_2]^{2+}$ in pH 7.3 phosphate buffer for 30 min (bottom). The mobile phase contained 5% acetonitrile, 0.10 M $NaH_2PO_4$, and sufficient $H_3PO_4$ to adjust the pH to 2.5. Peak assignments: A, solvent; B, solvent+$[Pt(en)_2Cl_2]^{2+}$+ $[Pt(en)_2]^{2+}$; C, 1; and D, oxidized form of 1.

This invention pertains to the discovery of a class of reagents that effectively form intramolecular disulfide bonds in peptides. Intramolecular disulfide bond formation is favored considerably over intermolecular disulfide bond formation. Thus, the formation of dimers or oligomers is substantially reduced. In addition, in preferred embodiments, the disulfide bond formation according to the methods of this invention occurs without reactions on the side chains of "susceptible amino acids (e.g., methionine, tyrosine and tryptophan).

In addition, unlike thallium(III) trifluroacetate, and other oxidants used for disulfide bond formation, the oxidation agents used in according to this invention are essentially non-toxic. In addition, the oxidants and their reaction products (e.g. $[Pt(en)_2Cl_2]^{2+}$, and its reduction product $[Pt(en)_2]^{2+}$, respectively) are essentially substitution inert under the conditions used for disulfide formation. They are also readily separated from peptides by HPLC. The reagents described herein are thus extremely well suited for the rapid and quantitative formation of intramolecular disulfide bonds in peptides.

In general, disulfide bond formation proceeds by providing one or more peptides where each peptide comprises at least two free sulfhydryl groups (e.g. comprises at least two cysteines). While the sulfhydryl groups are typically provided by the presence of cysteines, they can also be provided by other amino acids, particularly appropriately derivatized amino acids (e.g. penicillamine and homocysteine). Preferred peptides include chemically synthesized peptides, recombinantly expressed peptides, peptides isolated from a biological material (e.g. a biological fluid, a cell, a tissue, an organ, a bacterium or other prokaryote, a yeast or fungus, etc.) or a culture comprising a biological material (e.g. bioreactor). Suitable peptides also include, but are not limited to, peptides produced by the hydrolysis of various polypeptides or proteins. In particularly preferred embodiments, the peptides are chemically synthesized peptides.

Methods of chemically synthesizing peptides are well known to those of skill in the art. Where the desired peptides are relatively short the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology. Vol. 2: Special Methods in Peptide Synthesis*, Part a.; Merrifield, et al. (1963) *J. Am. Chem. Soc.*, 85: 2149–2156, and Stewart et al., (1984) *Solid Phase Peptide Synthesis*, 2nd ed. Pierce Chem. Co., Rockford, Ill.

The peptides used in the methods of this invention typically range in length from about 2 amino acids to about 200 amino acids, preferably from about 2 amino acids to about 100 amino acids, more preferably from about 2 amino acids to about 80 amino acids, and most preferably from about 2 amino acids to about 50 amino acids.

The methods generally involve contacting the peptides (or other molecules) with oxidizing reagents, as described below, under conditions whereby the sulfhydryl groups are oxidized to form a disulfide bond. Such conditions typically occur at a pH ranging from about pH 0 to about pH 9. In preferred embodiments, the reaction conditions are mildly acidic to neutral ranging from about pH 1 to about pH 8, and more preferably range from about pH 3 to about pH 6. The reaction is typically performed in any convenient buffer (e.g. phosphate buffer). In the case of $[Pt(en)_2Cl_2]^{2+}$, we have found it convenient to use a 2–10 mM stock solution of $[Pt(en)_2Cl_2]^{2+}$ in 1.00 M NaCl and phosphate buffer (pH 4–7) containing 1 mM EDTA. A solution of ca. 2 mM or less peptide (or crude peptide product cleaved from synthesis resin) is mixed with the $[Pt(en)_2Cl_2]^{2+}$ reagent in phosphate buffer, with $[Pt(en)_2Cl_2]^{2+}$ in slight excess. The mixture is allowed to react from 2 h (pH 4) to 30 min (pH 7), after which oxidation of the peptide to its disulfide form is complete.

In certain embodiments, the peptide is a dithiol peptide so that the disulfide linkage occurs only between the two cysteine present in the molecule. The methods can also be performed with peptides containing additional SH groups (e.g. cysteines). Where a cysteine (or other SH bearing amino acid) is present in the peptide, but it is desired to exclude that residue from disulfide bond formation, the SH can be derivatized with a protecting group (e.g. t-butyl (—$C(CH_3)$), trityl (—$C(C_6H_5)_3$) and acetamido ($CH_3CONH$—)) prior to reacting it with the reagents described herein.

In general synthetic peptide chemistries, the peptide will be fully or partially deprotected (at least the SH groups it is desired to incorporate into disulfide linkages). The deprotection can be prior to or after cleavage of the peptide from a solid support (in the case of solid phase syntheses) and the reaction creating the disulfide linkages can be performed in solution or in the solid phase.

Isolation/purification of Peptides.

Unlike previously known reagents, the reagents used in the present invention strongly favor the formation of intramolecular disulfide linkages over intermolecular linkages. Indeed, it was a surprising discovery that this preference for intramolecular disulfide linkage formation is so strong that it is not necessary to purify the peptide prior to disulfide linkage formation.

The reactions described herein can be performed on crude (chemically synthesized) peptide product, on crude recombinant peptide product, on naturally occurring peptides prior to elaborate isolation, on cleavage products of naturally occurring proteins, and the like. A single purification/cleanup step can then, optionally, be performed to remove undesired reaction products and unreacted peptides. Because, at most, a single purification procedure is used, peptide production using the methods of this invention is far more efficient and less costly than conventional approaches.

If desired, the peptide product can be separated from other components of the reaction mixture using standard purification methods. Methods of protein/peptide purification are well known to those of skill in the art and include, but are not limited to, ammonium sulfate precipitation, affinity chromatography, HPLC, FPLC, electrophoresis, capillary electrophoresis, 2-D TLC, and the like (see, generally, R. Scopes, (1982) *Protein Purification*, Springer-Verlag, N.Y.; Deutscher (1990) *Methods in Enzymology* Vol. 182: *Guide to Protein Purification*, Academic Press, Inc. N.Y.). One preferred purification protocol is illustrated in Example 1 and involves reversed-phase gradient HPLC on a 100 mm×250 mm C18 column with an acetonitrile-water mobile phase containing 0.1% TFA.

Reagents for the Formation of Disulfide Linkages.

As indicated above, this invention identifies reagents (oxidizing agents) that are particularly well suited to the formation of disulfide linkages in peptides. Particularly preferred reagents for this purpose are illustrated by Formula I:

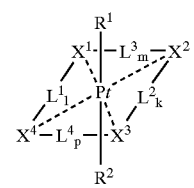

I.

where $R^1$ and $R^2$ are independently selected from the group consisting of Cl—, Br—, I—, OH—, and $RCO_2$— where R is an alkyl group or a substituted alkyl group (e.g., up to a 10 carbon alkyl group, preferably up to an 8 carbon alkyl group, more preferably up to a 6 carbon alkyl group, most preferably a 2, 3, 4, or 5 carbon alkyl group substituted or unsubstituted), Pt is Pt(fV); $X^1$, $X^2$, $X^3$, and $X^4$ are ligands independently selected from the group consisting of a nitrogen ligand (e.g. cyanide, ammonia, amine nitrogen, etc.), an oxygen ligand (e.g. carboxylate oxygen, etc.), a phosphorous ligand (e.g. phosphine phosphorous, etc.), a sulfur ligand (e.g. thioether sulfur, etc.), i, k, m, and p are independently 0 or 1; (i.e., one or more of the linkers is optionally present or absent), $L^1$, $L^2$, $L^3$, and $L^4$ when present, are independently selected linkers.

In various embodiments, $X^1$, $X^2$, $X^3$, and $X^4$ are all the same or one or more differ from the others. In particularly preferred embodiments, $X^1$, $X^2$, $X^3$, and $X^4$ are all the same. Similarly in various embodiments, $R^1$ and $R^2$ are the same or different, but in particularly preferred embodiments, $R^1$ and $R^2$ are the same.

In certain particularly preferred embodiments, $L^1$ and $L^2$ are the same and/or $L^3$ and $L^4$ are the same. In certain instances $L^1$ and $L^2$ are absent and/or $L^3$ and $L^4$ are absent. In certain some embodiments, where $L^1$, $L^2$, $L^3$, and $L^4$ are all present, $X^1$—$L^3$—$X^2$—$L^2$—$X^3$—$L^4$—$X^4$—$L^1$ form a ring (e.g. $H_2NCH_2CH_2NHCH_2CH_2NHCH_2CH_2NH_2$).

In some particularly preferred embodiments, $L^1$, $L^2$, $L^3$ and $L^4$ are all absent and $X^1$, $X^2$, $X^3$, and $X^4$ are cyanide or ammonia. In such instances, $R^1$ and $R^2$ are the same or different, but most preferably, are the same.

In one group of embodiments, $L^1_i$ and $L^2_k$ are present (i.e., i and k are 1) and are alkyl linkers, substituted alkyl linkers, or aromatic linkers (e.g., including up to a 10 carbon alkyl or aromatic linker, preferably up to an 8 carbon alkyl or aromatic linker, more preferably up to a 6 carbon alkyl or aromatic linker, most preferably a 4, or 5 carbon alkyl or aromatic linker or 2, or 3 carbon alkyl group linker any of which can be substituted or unsubstituted). In particularly preferred embodiments, $L^1_i$ and $L^2_k$ are alkyl linkers comprising from 1 to 4 carbons. In particularly preferred versions of such embodiments, $R^1$ and $R^2$ are the same or different and include, but are not limited to, Cl—, Br—, or I—.

Disulfide linkage forming reagents of this invention that are particularly useful in peptide synthesis include, but are not limited to, compounds where $L^3$ and $L^4$ are absent and —$X^1$—$L^1$i-$X^4$— and —$X^2$—$L^2_k$—$X^3$— are both the same with $L^1$ and $L^2$ being a one to four carbon linker, more preferably a two carbon linker (e.g., —$CH_2$—$CH_2$—) and $X^1$, $X^2$, $X^3$, and $X^4$ are amino or cyanide (e.g. where —$X^1$—$L^1$i-$X^4$— and —$X^2$—$L^2_k$—$X^3$— are both: —$NH_2CH_2CH_2NH_2$—). $R^1$ and $R^2$ are as described above, but in one most preferred embodiment the reagent is $[Pt(en)_2Cl_2]^{2+}$. Another highly preferred reagent, particularly were the peptide lacks a methionine is $[Pt(CN)_4C_2]^{2-}$. In both cases, the Cl— is easily substituted with I—, Br—, and the like.

In general, two major design considerations underlie the selection of reagents for use in the methods of this invention. First, the constituent molecules ($X^1$–$X^4$, $L^1$–$L^4$) are preferably kinetically stable on platinum, that is they cannot easily be replaced.

A major design consideration so that the oxidation that forms the disulfide linkage occurs, but the redox potential of the complex is sufficiently low that undesired side reactions (e.g. oxidation of methionine) are eliminated. One preferred approach is to block the equatorial coordination sites to avoid reaction of the product Pt(II) complex with other functional groups of the peptide.

One of skill in the art will appreciate that a number of the compounds used as disulfide linkage forming reagents in this invention are commercially available (e.g. dimethylsulfoxide (DMSO), ferricyanide (Fe(CN)63-)) or are readily derivable from commercially available precursors. Thus, for example $[Pt(en)_2Cl_2]Cl_2$ was prepared from $[Pt(en)_2]CL^2$ (available from Aldritch) according to standard methods well known to those of skill in the art (see, e.g., Basolo et al. (1950) *J. Am. Chem. Soc.* 72: 2433–2438, Poë (1963) *J. Chem. Soc.* 183–188.

Similarly, $K_2[Pt(Cn)_4Cl_2]$ is synthesized according to the procedure of Shi and Elding (1998) *J. Inorg. Chim. Acta*, 282; 55–60, (see also Shi and Rabenstein (1998) *J. Org. Chem.*, 64: 459–4595). Other species are also readily synthesized by modification of these protocols or routine substitutions into generally available precursors.

Methods of Making Peptides.

In certain embodiments, this invention contemplates the use of the disulfide-linkage forming reagents described herein in various peptide manufacturing contexts. In preferred embodiments, the methods are used in conjunction with automated chemical peptide synthesis (e.g. peptide synthesis as described by Merrifield, et al. (1963) *J. Am. Chem. Soc.*, 85: 2149–2156, and Stewart et al., (1984) *Solid Phase Peptide Synthesis*, 2nd ed. Pierce Chem. Co., Rockford, Ill.). As indicated above, the disulfide linkage forming reaction is performed after deprotecting at least the protected SH groups that are to participate in the desired reaction. In the case of solid phase synthesis, the deprotection can occur prior to or after cleavage of the peptide from the supporting resin.

Thus, in one embodiment, this invention contemplates formation of the disulfide linkages on a peptide synthesizer. In this context, it is effective to provide the disulfide linkage forming reagent(s) in one or more vials on the peptide synthesizer. This can be accomplished with a wide variety of commercially available peptide synthesizers. In addition, methods of manufacturing and/or modifying peptide synthesizers are well known to those of skill in the art (see, e.g., U.S. Pat. Nos. 5,453,487, 5,380,495, 5,362,447, 5,344,613, 4,861,866, 4746,490, and the like). The machines described in such patents and known to those of skill in the art can readily be adapted to incorporate the reagents and methods of this invention.

Other Suitable Substrates.

While peptides are the preferred "substrate" for the methods of this invention, it will be appreciated that the methods are not so limited. Essentially any molecule comprising two or more sulfhydryl groups that can be juxtaposed sufficiently close together to form a disulfide linkage are suitable. Such molecules include, but are not limited to recombinantly expressed and naturally occurring proteins and polypeptides, various antibodies, glycoproteins, thiolated oligonucleotides, chimeric nucleic acid/peptide molecules, organic dithiol (or polythiol) compounds, and the like.

The suitability of a particular substrate for the methods of this invention can readily be ascertained with essentially minimal experimentation. The "substrate" in question is reacted as described herein and then assayed for the presence or absence of disulfide linkages. A reaction efficiency can be determined and the reaction mixture can be evaluated for undesired reaction products. This procedure is illustrated for peptides in detail in Example 1.

Kits.

In another embodiment this invention provides kits for forming an intramolecular disulfide bond in a peptide. Preferred kits comprise a container containing one or more of the compounds according to Formula I as described herein. The kits also optionally include instructional materials providing a protocol teaching the use of the compounds described herein as a reagent to form an intramolecular disulfide bond in a peptide. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In various embodiments, the compound may be provided as a dry reagent e.g. a lyophilized powder), or in solution (e.g. in a buffer at a pH ranging from about pH 1 to about pH 9, more preferably at a pH ranging from about pH 3 to about pH 7).

The kits optionally include additional reagents and devices for the creation of peptides having intramolecular disulfide bonds. Such devices include, but are not limited to measuring devices, reagent vials suitable for mounting on automated chemical peptide synthesizers, reagents and/or columns, and/or buffers for protein purification, solvents for dissolving the compounds described herein, and the like.

The kits may also include instruction sets, programs, programming instructions and the like to instruct a commercial peptide synthesizer to perform the reaction for disulfide linkage formation according to the methods of this invention.

EXAMPLES

The following examples are offered to illustrate, but not to limit the claimed invention.

Example 1
Discovery of a Highly Selective and Efficient Reagent for Formation of Intramolecular Disulfide Bonds in Peptides This example demonstrates that trans-$[Pt(en)_2Cl_2]^{2+}$ (en=ethylenediamine) is a highly selective and efficient reagent for the quantitative formation of intramolecular disulfide bonds in peptides. A series of fourteen dithiol peptides which form disulfide-containing rings ranging in size from 14 to 53 atoms were used to characterize the reagent. The dithiol peptides are cleanly and rapidly converted to their disulfide forms by a slight excess of the platinum complex under mild reaction conditions (slightly acidic and neutral media). For all the dithiol peptides studied, including a penicillamine-derived peptide, the oxidation yields range from 97% to 100%. No side reactions were observed, including no oxidation of the methionine side chain. The reaction kinetics for oxidation of reduced pressinoic acid were found to be second-order overall: Rate=k'[Pt(IV)][dithiol peptide], where k' is a pH-dependent second-order rate constant. Values of 0.60±0.01, 3.5±0.2 and 22±1 $M^{-1}s^{-1}$ were determined for k' at pH 3.0, 4.0 and 5.0, respectively (25° C. and 0.45 M ionic strength). A reaction mechanism for oxidation of dithiol peptides by $[Pt(en)_2Cl_2]^{2+}$ is proposed.

$[Pt(en)_2Cl_2]^{2+}$ and its reduction product $[Pt(en)_2]^{2+}$ are essentially substitution inert under the conditions used for disulfide formation, they are nontoxic and they are readily separated from peptides by HPLC. The characteristics of $[Pt(en)_2Cl_2]^{2+}$ and its reaction properties with dithiol peptides suggest that $[Pt(en)_2Cl_2]^{2+}$ is a universal reagent for the rapid and quantitative formation of intramolecular disulfide bonds in peptides.

We have demonstrated that trans-$[Pt(CN)_4Cl_2]^{2-}$ is an efficient reagent for the rapid and quantitative oxidation of dithiol peptides to their disulfide forms.[6] Oxidation takes place by a $Cl^+$ atom transfer mechanism. Unfortunately, $[Pt(CN)_4Cl_2]^{2-}$ is a sufficiently strong oxidizing agent (E°'= 0.926 V (Goldberg and Helper (1968) *Chem. Rev.* 68: 229–252)) that it also oxidizes methionine to methionine sulfoxide (Shi and Rabenstein (1999) *J. Org. Chem.* 64: 4590–4595; Shi et al. (1997) *J. Chem. Soc., Dalton Trans.* 2073–2077). However, this was the only side reaction observed for an otherwise excellent reagent for formation of intramolecular peptide disulfide bonds, which encouraged us to investigate other trans-dichloro-Pt(IV) complexes; the idea being that by tuning down the redox potential of the complex, it may be possible to eliminate this side reaction while still maintaining the rapid and quantitative nature of the reaction. A major design consideration was that the equatorial coordination sites should be blocked to avoid reaction of the product Pt(II) complex with other functional groups of the peptide. In this example, we report that, by pursuing this design approach, we have discovered that trans-$[Pt(en)_2Cl_2]^{2+}$ (en=ethylenediamine, $[Pt(en)_2Cl_2]^{2+}$/$[Pt(en)_2]^{2+}$=0.58 V (Bard et al. (1985) pp. 345–365 In: *Standard Potentials in Aqueous Solution*, Marcel Dekker: N.Y.)) is a highly selective and efficient reagent for formation of intramolecular disulfide bonds in peptides without any observed side reactions. Further, the reaction conditions are mild and the Pt(IV) and its Pt(II) reduction product $[Pt(en)_2]^{2+}$ are nontoxic and readily separable from peptides, which are desirable properties for a disulfide bond-forming reagent (Andreu et al., supra; Moroder et al., supra; Annis and Barany, supra.; Tam et al. (1991) *J. Am. Chem. Soc.* 11:, 6657–6662; Annis and Barany (1998) *J. Am. Chem. Soc.*, 120: 7226–7238). These properties together with the results presented here indicate that the discovery of $[Pt(en)_2Cl_2]^{2+}$ as a disulfide bond-forming reagent represents a particularly significant development in the seach for efficient methods for formation of intrapeptide disulfide bonds.

Results and Discussion

The dithiol peptides used in the present study (Table 1) range from 4 to 20 amino acid residues in length and the loop sizes of the oxidized disulfide forms vary from 14 to 53-membered rings.

TABLE 1

Dithiol Peptides Used in the Study to Characterize the Disulfide-Bond Forming Properties of $[Pt(en)_2Cl_2]^{2+}$.

| No. | Sequence of dithiol peptides | ring size[a] | oxidation yield[b] | SEQ ID NO |
|---|---|---|---|---|
| 1 | Ac-Cys-Gly-Pro-Cys-$NH_2$ | 14 | 100% | 1 |
| 2 | Ac-Cys-Pro-Phe-Cys-$NH_2$ | 14 | 97% | 2 |
| 3 | Ac-Thr-Cys-Pro-Phe-Cys-Arg-$NH_2$ | 14 | 100% | 3 |
| 4 | Ac-Pro-Thr-Cys-Pro-Phe-Cys-Arg-Lys-$NH_2$ | 14 | 100% | 4 |
| 5 | Ac-Lys-Pro-Thr-Cys-Pro-Phe-Cys-Arg-Lys-Thr-$NH_2$ | 14 | 100% | 5 |
| 6 | Ac-Thr-Asp-Ile-Thr-Cys-Gly-Tyr-Cys-His-Lys-Leu-His-$NH_2$ | 14 | 100% | 6 |
| 7 | Ac-Cys-Pro-Phe-Ala-Ala-Cys-$NH_2$ | 20 | 100% | 7 |
| 8 | Cys-Tyr-Phe-Gln-Asn-Cys (reducedpressinoicacid) | 20 | 100% | 8 |
| 9 | Cys-Tyr-Ile-Gln-Asn-Cys-Pro-Leu-Gly-$NH_2$ (reducedoxytocin) | 20 | 98% | 9 |
| 10 | Cys-Tyr-Phe-Gln-Asn-Cys-Pro-Arg-Gly-$NH_2$ (reducedarginine-vasopressin) | 20 | 100% | 10 |
| 11 | Ala-Gly-Cys-Lys-Asn-Phe-Phe-Trp-Lys-Thr-Phe-Thr-Ser-Cys (reducedsomatostatin) | 38 | 99% | 11 |
| 12 | Arg-Pro-Cys-Pro-Gln-Cys-Phe-Tyr-Pro-Leu-Met-$NH_2$ | 14 | 99% | 12 |
| 13 | Cys-Phe-Gly-Ser-Arg-Ile-Asp-Arg-Ile-Gly-Ala-Gln-Ser-Gly-Met-Gly-Cys-Gly-Arg-Phe | 53 | 100% | 13 |
| 14 | HSC(Me)$_2$CH$_2$CO-Tyr(Me)-Phe-Gln-Asn-Cys-Pro-Arg-Gly-$NH_2$[c] | 20 | 97% | 14 |

[a]Ring members for the oxidized forms. [b]Oxidation yield is reported for the single step of conversion of dithiol peptides to their disulfide forms with slight excess of platinum(IV) complex. [c]Reduced form of [1-deaminopenicillamine, 2-(O-methyl)tyrosine]arginine-vasopressin.

Peptides 1–7.

Peptide 1–6 are model compounds for the active site of thioredoxin (1) (Holmgren (1985) *Ann. Rev. Biochem.*, 54: 237–271), glutathione thioltransferase (2–5) (Gan and Wells (1986) *J. Biol. Chem.* 261: 996–1001), and the disulfide bond-forming protein DsbC (6) (Zapun et al. (1995) *Biochemistry* 34: 5075–5089). Peptide 7 is derived from peptide 1, with two additional alanine residues to increase the loop size in the oxidized form. Reaction of peptides 1–7 with $[Pt(en)_2Cl_2]^{2+}$ to form the intramolecular disulfide bond was monitored by isocratic reversed phase HPLC. To illustrate, FIG. 1 gives results for the oxidation of 1. The top chromatogram is for a freshly prepared 80 μM solution of 1; the bottom chromatogram is for the products obtained after reaction of 80 μM 1 and 150 μM [Pt(en)$_2$Cl$_2$]$^{2+}$ in pH 7.3 phosphate buffer for 30 min. The peak assignments given in the egend to FIG. 1 for [Pt(en)$_2$Cl$_2$]$^{2+}$ and [Pt(en)$_2$]$^{2+}$ are based on chromatograms for uthentic samples. The broad peak at 23.2 mm is assigned to the disulfide form of 1 based on the mass spectrometric results (Theoretical: 416.5, Found: 417). The broad peak for the disulfide form is ascribed to the slow cis-trans isomerization of the glycine-proline peptide bond and a relatively high population of the cis isomer (Larive and Rabenstein (1993) *J. Am. Chem. Soc.*, 115: 2833–2836). The bottom chromatogram was also run for a longer time than shown in FIG. 1; no late-eluting peaks we re observed. The chromatograms in FIG. 1 indicate that a slight excess of [Pt(en)$_2$Cl$_2$]$^{2+}$ cleanly and rapidly transforms 1 to its intramolecular disulfide form. It was determined from the HPLC response factor that the transformation is quantitative (Table 1). Chromatographic patterns for the products of the oxidation of peptides 2–7 are similar to that for 1 except that peaks for the disulfide forms are sharp, cf. Supporting Information.

Reduced Peptide Hormones 8–11.

Figure 2:
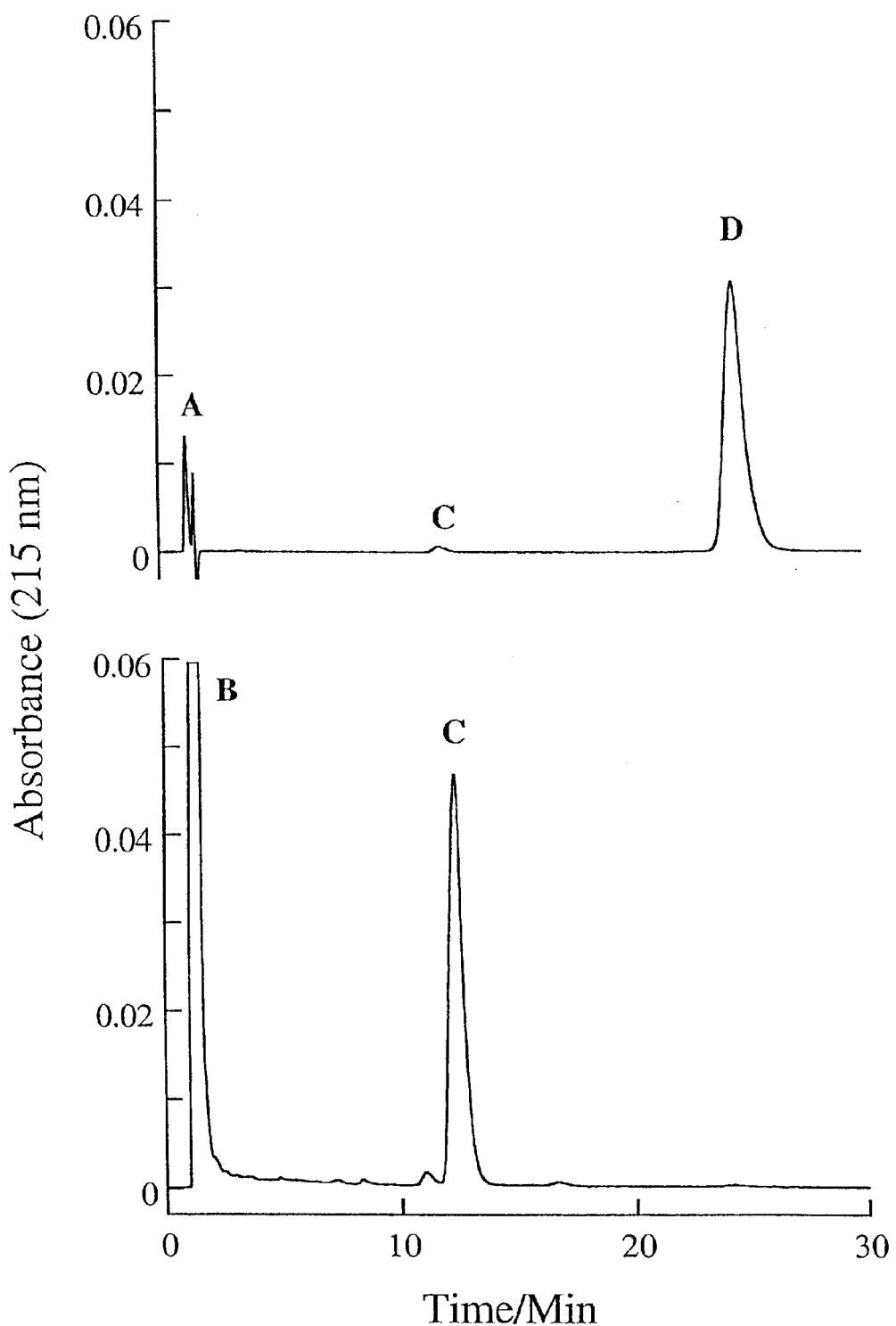
FIG. 2 shows chromatograms of 100 $\mu$M 8 (top) and a reaction mixture of 100 $\mu$M 8 and 150 $\mu$M $[Pt(en)_2Cl_2]^{2+}$ in a pH 7.3 phosphate buffer after reaction for 30 min (bottom). The mobile phase contained 12% acetonitrile, 0.10 M $NaH_2PO_4$, and sufficient $H_3PO_4$ to adjust the pH to 2.5. Peak assignments: A, solvent; B, solvent+$[Pt(en)_2Cl_2]^{2+}$ +$[Pt(en)_2]^{2+}$; C, oxidized form of 8; and D, 8.

Peptides 8–11 are the reduced forms of the disulfide-containing hormones pressinoic acid, oxytocin, arginine-vasopressin, and somatostatin, respectively. FIG. 2 presents results for oxidation of peptide 8 by [Pt(en)$_2$Cl$_2$]$^{2+}$. The top chromatogram is for a freshly prepared 100 μM solution of 8. The bottom chromatogram is for a reaction mixture of 100 μM 8 and 150 μM [Pt(en)$_2$Cl$_2$]$^{2+}$ in pH 7.3 phosphate buffer after 30 min of reaction. The peak at 15.7 min in the bottom chromatogram was assigned to the oxidized form of 8 by comparison to the chromatogram of an authentic sample of pressinoic acid. Peak area measurements indicate that conversion of 8 to its disulfide form is quantitative. The reaction of [Pt(en)$_2$Cl$_2$]$^{2+}$ with peptides 9–11 was also found to be rapid and quantitative for these reaction conditions, cf. Supporting Information.

In previous syntheses of oxytocin and arginine-vasopressin and their derivatives (Hope et al. (1962) *J. Biol. Chem.* 237: 1563–1566; Hruby et al. (1977) *J. Org. Chem.* 42: 3552–3556; Live et al. (1977) *J. Org. Chem.* 42: 3556–3561; Moore (1978) *Biochem. J.* 173: 403–409), it was reported that oxidation of the dithiol groups by ferricyanide results predominantly, but not exclusively, in formation of intramolecular disulfide bonds. This, however, was not the case for the related hexapeptides, tocinamide and pressinamide (Moore (1978) *Biochem. J.* 173: 403–409). Oxidation of the dithiol forms of tocinamide and pressinamide by ferricyanide results mainly in the formation of dimers and higher polymers (Id.). In contrast, reaction with [Pt(en)$_2$Cl$_2$]$^{2+}$ results in the quantitative formation of intramolecular disulfide bonds, regardless of the peptide sequence.

Methionine-containing Peptides 12 and 13.

Figure 3:
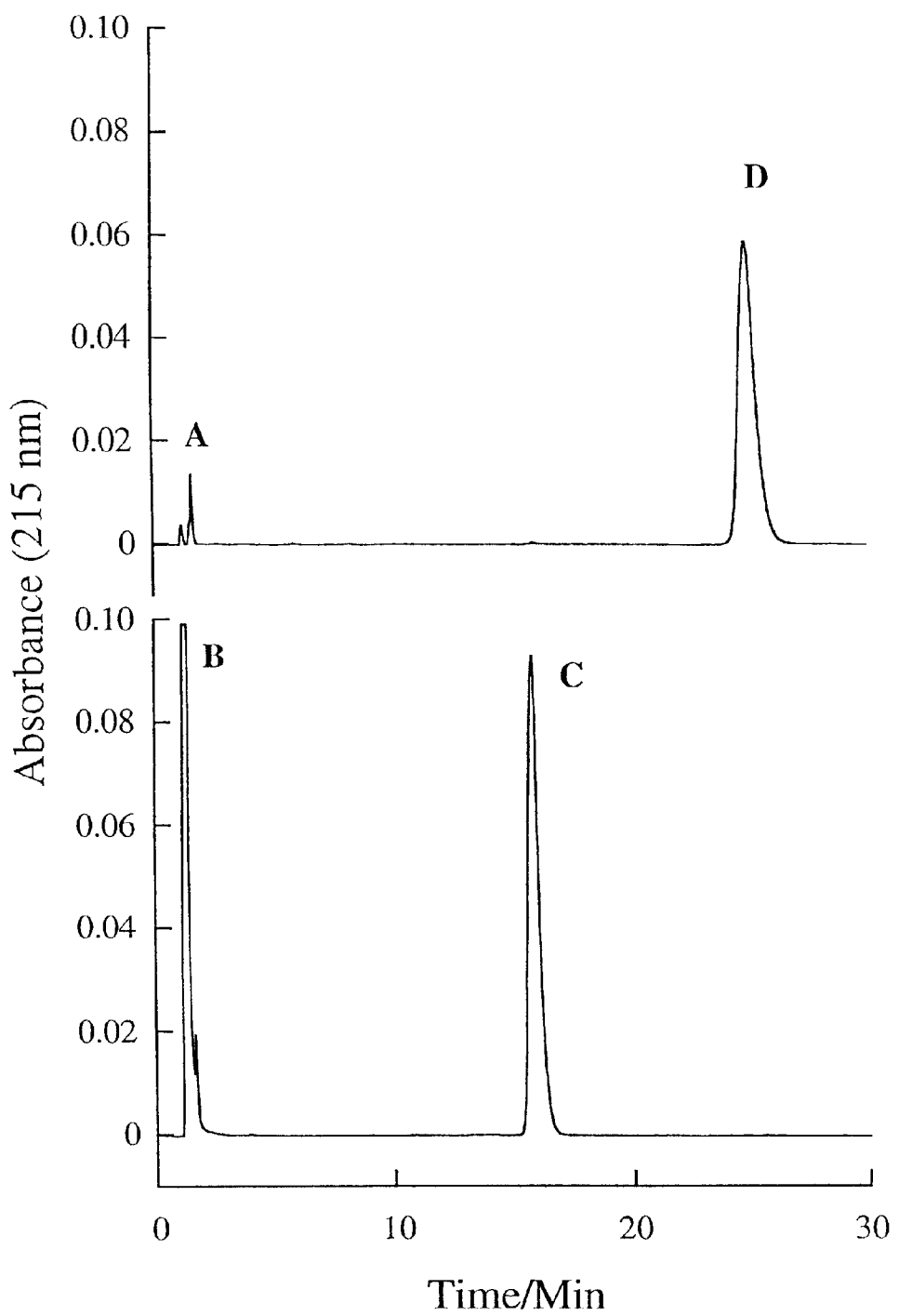
FIG. 3 shows chromatograms of 40 $\mu$M 13 (top) and the products from the reaction of 40 $\mu$M 13 and 150 $\mu$M $[Pt(en)_2Cl_2]^{2+}$ in pH 6.0 phosphate buffer for 30 min (middle) and 10 h (bottom). The mobile phase contained 20% acetonitrile, 0.10 M $NaH_2PO_4$, and sufficient $H_3PO_4$ to adjust the pH to 2.5. Peak assignments: Peak assignments: A, solvent; B, solvent+$[Pt(en)_2Cl_2]^{2+}$+$[Pt(en)_2]^{2+}$; C, 13; and D, oxidized form of 13.

Peptides 12 and 13 are the dithiol forms of the methionine-containing peptides [Cys (Munson and Barany (1993) *J. Am. Chem. Soc.* 115: 10203–10216; Shi and Rabenstein (1999) *J. Org. Chem.* 64: 4590–4595), Tyr (Goldberg and Helper (1968) *Chem. Rev.* 68: 229–252), Pro (Shi et al. (1997) *J. Chem. Soc., Dalton Trans.* 2073–2077)]-Substance P (selective NK-1 agonist) and Atrial Natriuretic Factor (ANF, 11–30, frog), respectively (Lavielle et al. (1988) *J. Biochem. Pharmacol.* 37: 41–49; Lazure et al. (1988) *FEBS Letters*, 238: 300–306). FIG. 3 shows chromatograms for the oxidation of 13 in a phosphate buffer at pH 6.0; peak assignments and reaction conditions are given in the figure legend. The top chromatogram is for a fresh solution of 40 μM 13, the middle and bottom chromatograms are for a mixture of 40 μM 13 and 150 μM [Pt(en)$_2$Cl$_2$]$^{2+}$ in pH 6.0 phosphate buffer after 30 min and 10 h of reaction, respectively. The peak at 23.7 min is assigned to the oxidized form based on its retention time being identical to that for an authentic sample and the molecular weight of the isolated peptide: (Theoretical: 2116.6; Found: 2116). As determined by HPLC analysis, 100% of the dithiol peptide was converted to the disulfide form after reaction for 30 min. Also, the excess [Pt(en)$_2$Cl$_2$]$^{2+}$ and the Pt(II) product in the reaction mixture did not interact with the oxidized peptide including the methionine side chain, as evidenced by the fact that the chromatogram obtained after 10 h of reaction was identical to that obtained after 30 min of reaction. Similar results were obtained for peptide 12, which also contains a methionine residue. Formation of the 53-membered disulfide-containing ring in the oxidized form of peptide 13, and also the 38-membered ring in 11, was found to be as fast and clean as formation of the much smaller rings in peptides 1–7.

Oxidation yields, which range from 97% to 100%, are given in Table 1. It is noteworthy that the peptides studied include all the amino acids with readily oxidizable side chains (methionine, tyrosine, and tryptophan). Thus, the oxidation of dithiol peptides to their disulfide forms by [Pt(en)$_2$Cl$_2$]$^{2+}$ is quantitative, with no known side reactions. The oxidation reaction can be described by Eq 1.

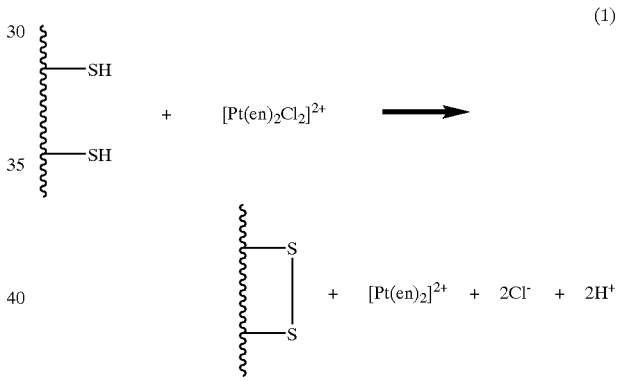

(1)

Peptide 14.

Figure 4:
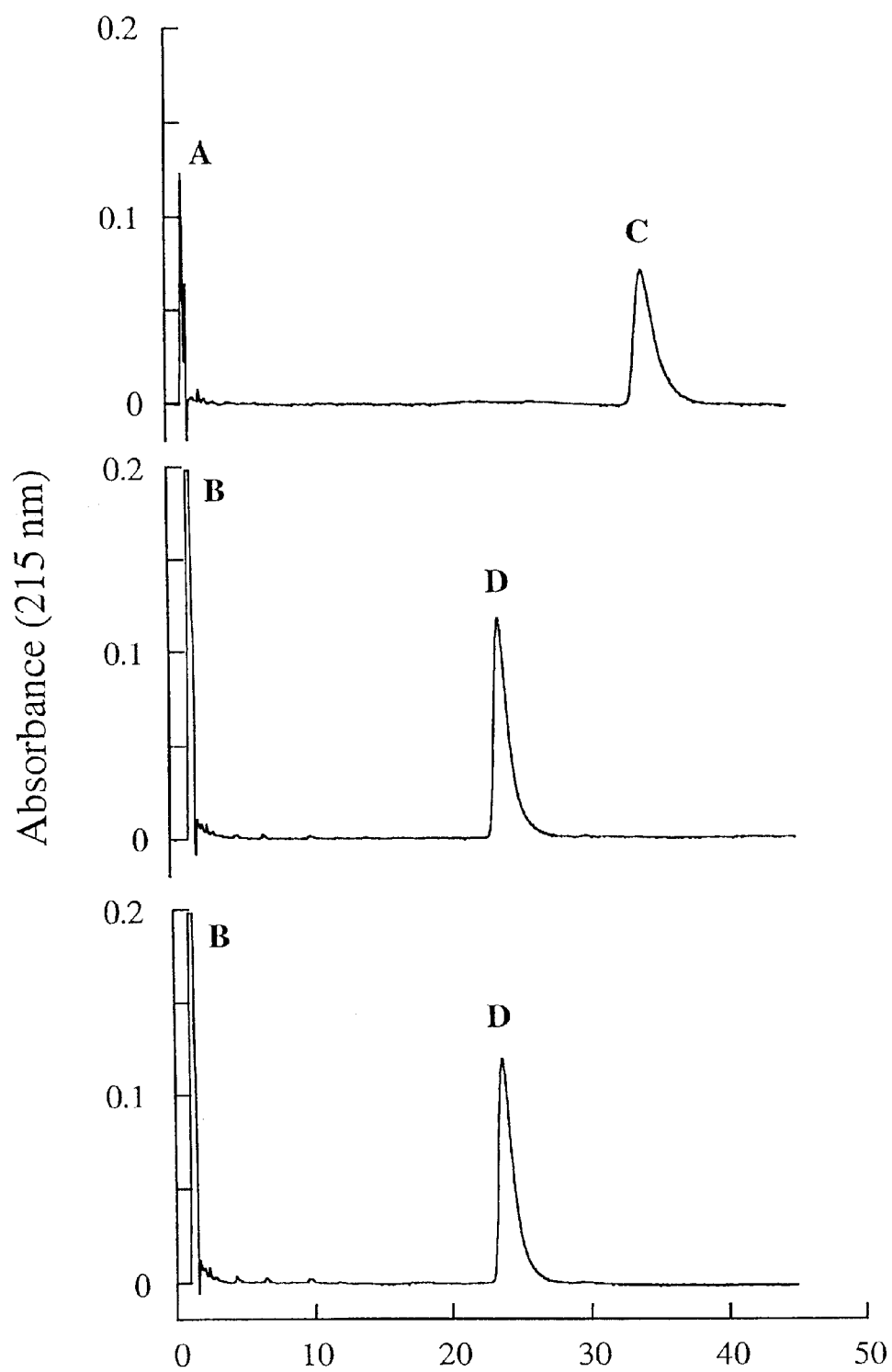
FIG. 4 shows chromatograms of 100 $\mu$M 14 (top) and the products from the reaction of 100 $\mu$M 14 and 200 $\mu$M $[Pt(en)_2Cl_2]^{2+}$ in pH 4.0 phosphate buffer for 1.5 h (bottom). The mobile phase contained 24% acetonitrile, 0.10 M $NaH_2PO_4$, and sufficient $H_3PO_4$ to adjust the pH to 2.5. Peak assignments: Peak assignments: A, solvent; B, solvent+$[Pt (en)_2Cl_2]^{2+}$+$[Pt(en)_2]^{2+}$; C, 14; and D, oxidized form of 14. Minor peaks at 11.0 and 16.7 min are probably from side reaction products, cf. text.

The oxidation of dithiol peptides by [Pt(en)$_2$Cl$_2$]$^{2+}$ was extended to penicillamine-derived peptide 14 (Bankowski, and Manning (1978) *Med. Chem.* 21: 850–853); the purpose being to examine the oxidation efficacy when steric hindrance near the thiol groups is increased. FIG. 4 shows results for oxidation of 14; the reaction conditions are given in the figure caption. The bottom chromatogram was also run for a longer time; no late-eluting peaks were observed. The peak at 12.3 min was assigned to the disulfide form of 14 by comparison to the retention time of an authentic sample. It is of interest to note that, although steric hindrance due to the introduction of a deamino-penicillamine increases the difficulty for ring closure, formation of the disulfide form of 14 (yield 97%) is still the predominant reaction. However, some minor peaks (ca. 3%) are observed in FIG. 4, which are probably due to side products as discussed below.

Reaction Conditions.

The oxidation reaction was studied under various conditions. To determine if it is necessary to isolate the dithiol peptide in pure form before formation of the disulfide bond, [Pt(en)$_2$Cl$_2$]$^{2+}$ was reacted directly with the crude product obtained by cleavage of peptide 6 from solid-phase peptide synthesis resin and deprotection of side chain functional groups (vide infra). Chromatograms obtained by semi-preparative HPLC for a reaction mixture containing ca 2 mM 6 and 3 mM [Pt(en)$_2$Cl$_2$]$^{2+}$ (phosphate buffer at pH 6.0, reaction time 30 min) indicate that 6 is rapidly oxidized to its disulfide form, as identified by mass spectrometry, cf. Supporting Information. No additional peaks due to dimer or polymers of 6 were observed, which indicates that oxidation is s till clean and quantitative even at millimolar peptide concentratinons.

The rate of formation of the intramolecular disulfide bond by reaction with [Pt(en)$_2$Cl$_2$]$^{2+}$ is pH dependent. Formation of the disulfide bond by reaction of 100 $\mu$M 8 with 250 $\mu$M [Pt(en)$_2$Cl$_2$]$^{2+}$ was found to be complete in 3 h, 20 min, 3 min and 20 sec at pH 4.0, 5.0, 6.0 and 7.0, respectively, at room temperature. No peaks were detected from side products, even for the pH 7.0 conditions where the reaction took place very rapidly.

To determine if [Pt(en)$_2$Cl$_2$]$^{2+}$ can be used to form disulfide bonds in peptides which are only slightly water-soluble but are soluble in aqueous-organic mixtures, the oxidation of 13 was studied in aqueous/acetonitrile solution. Peptide 13 was found to be cleanly and quantitatively oxidized in aqueous phosphate buffer containing up to 50% acetonitrile. [Pt(en)$_2$Cl$_2$]$^{2+}$ is soluble at the millimolar level in mixed aqueous/organic solvent mixtures with methanol, ethanol, acetonitrile, and acetone.

Kinetics and Reaction Mechanism.

Figure 5:
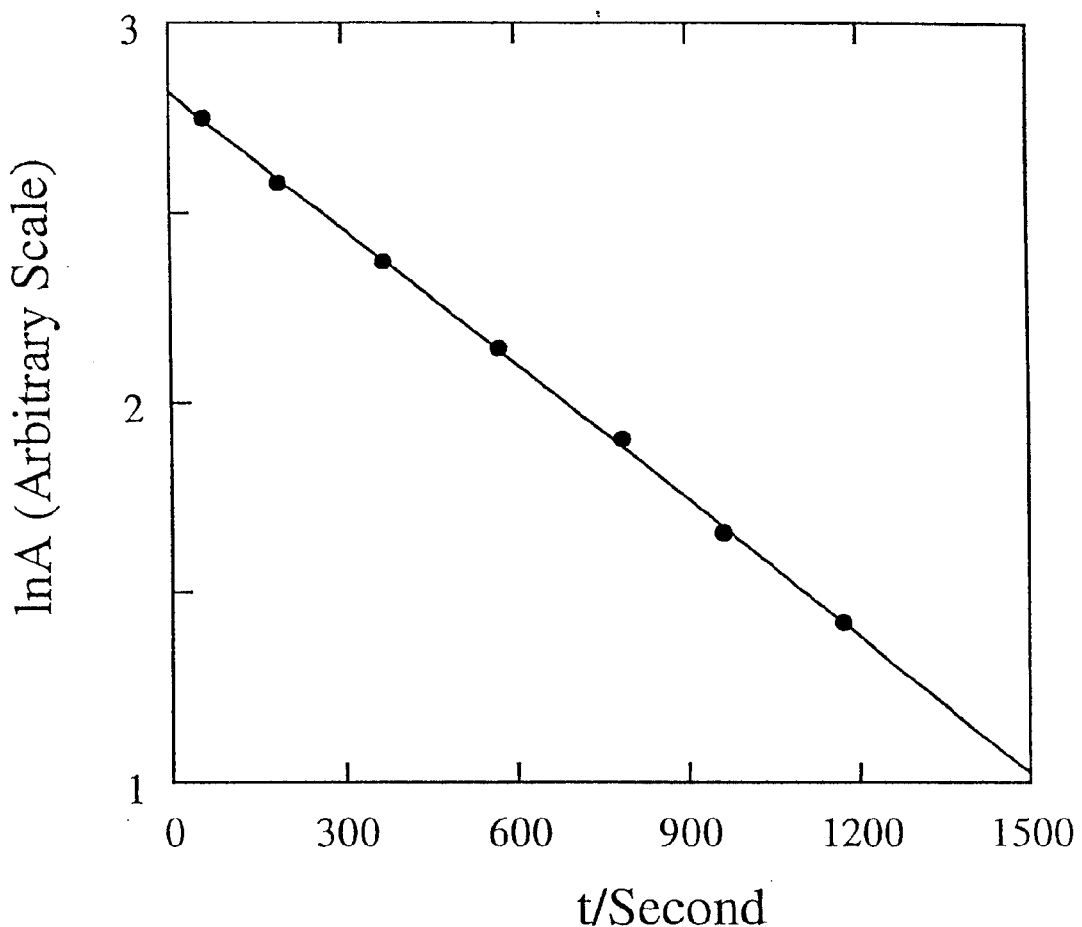
FIG. 5 shows a plot of lnA versus reaction time according to Eq 2 for oxidation of peptide 8 by $[Pt(en)_2Cl_2]^{2+}$ in pH 3.0 phosphate buffer. Reaction conditions: [8]=80 $\square$M, [Pt (IV)]=2.00 mM, ionic strength of 0.45 M and 25° C.

The kinetics of the reaction of peptide 8 with [Pt(en)$_2$Cl$_2$]$^{2+}$ were studied. The oxidation reaction was followed by isocratic HPLC by monitoring the disappearance of 8 under pseudo-first-order conditions with [Pt(en)$_2$Cl$_2$]$^{2+}$ present in a 10-fold or larger excess. Because 8 can be totally converted to its disulfide form by reaction with [Pt(en)$_2$Cl$_2$]$^{2+}$ (FIG. 2), the decrease in the area of the peak for 8 vs time can be described by Eq 2 if the reaction is first-order in 8, $$\ln A = \ln A_0 - k_{obsd} t \quad (2)$$

where $A_0$ and $A$ are the peak areas of 8 at the start of the reaction and at time t, respectively. Plots of lnA versus time are linear, as shown in FIG. 5 for pH 3 data, which indicates that the reaction is indeed first-order in 8; a pseudo-first-order rate constant of $k_{obsd}$=1.20×10$^{-3}$ s$^{-1}$ was obtained from the linear plot in FIG. 5.

Figure 6:
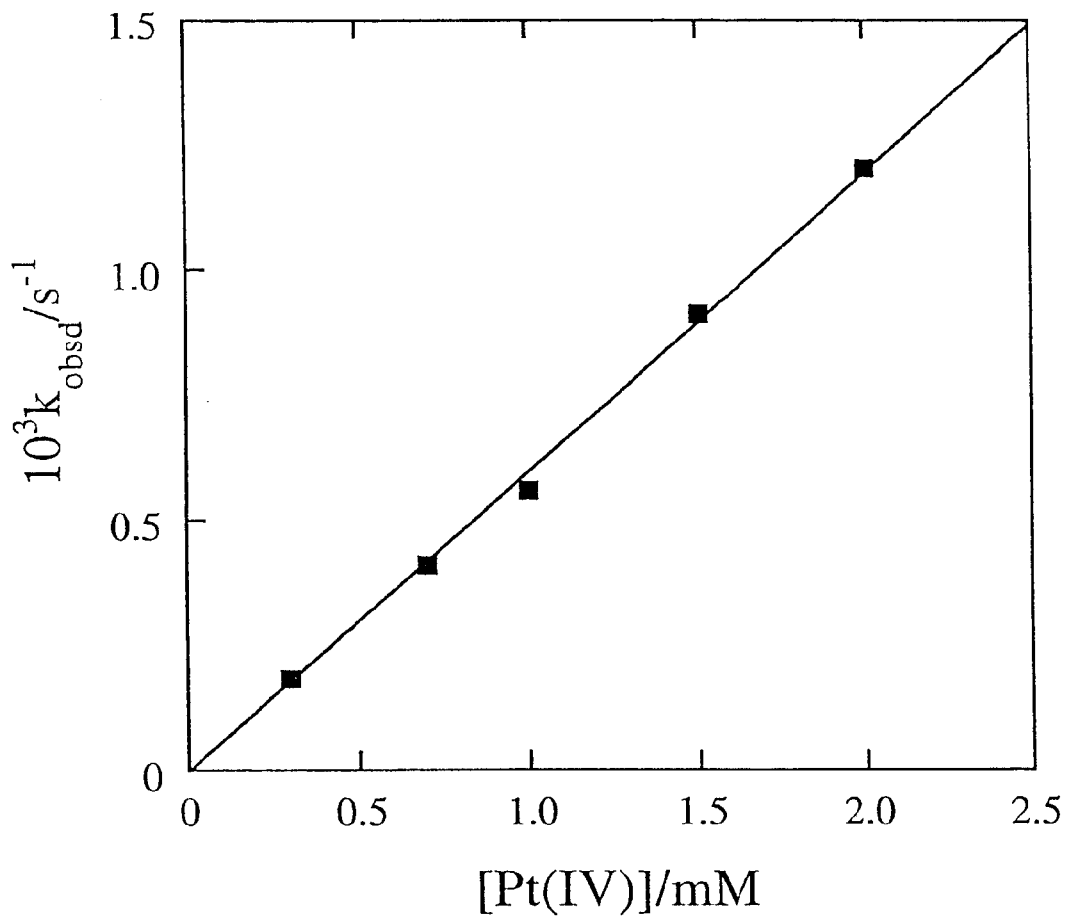
FIG. 6 shows a plot of $k_{obsd}$ versus [Pt(IV)] according to Eq 3 for reaction between peptide 8 and $[Pt(en)_2Cl_2]^{2+}$ at pH 3.0, 25° C. and ionic strength of 0.45 M.

To determine the order of the reaction with respect to [Pt(en)$_2$Cl$_2$]$^{2+}$, the concentration of [Pt(en)$_2$Cl$_2$]$^{2+}$ in a pH 3.0 reaction mixture containing 30–80 $\mu$M 8 was varied from 0.30 to 2.50 mM. The dependence of $k_{obsd}$ on [Pt(en)$_2$Cl$_2$]$^{2+}$ is linear with a zero intercept, as shown in FIG. 6, which demonstrates that the oxidation reaction is also first-order with respect to the [Pt(en)$_2$Cl$_2$]$^{2+}$. Thus, the oxidation reaction follows an overall second-order rate law as described by Eq 3, where k' denotes the pH-dependent second-order rate const ant. Values of 0.60±0.01, $$-d[8]/dt = k_{obsd}[8] = k'[Pt(IV)][8] \quad (3)$$

3.5±0.2 and 22±1 M$^{-1}$s$^{-1}$ were determined for k' at 25° C. and ionic strength 0.45 M at pH 3.0, 4.0, and 5.0, respectively. The reaction is too fast to be followed by HPLC at pH$\geq$6. The oxidation reaction was also studied in 1.00 M HCl; the reaction of 60 $\mu$M 8 with 1.00 mM [Pt(en)$_2$Cl$_2$]$^{2+}$ yielded ca. 4% and 10% oxidized peptide after 4 h and 10 h, respectively, at room temperature. The yields are comparable to those obtained by air oxidation, which suggests that the reaction of [Pt(en)$_2$Cl$_2$]$^{2+}$ with fully protonated peptide 8 is negligibly slow.

Figure 7:
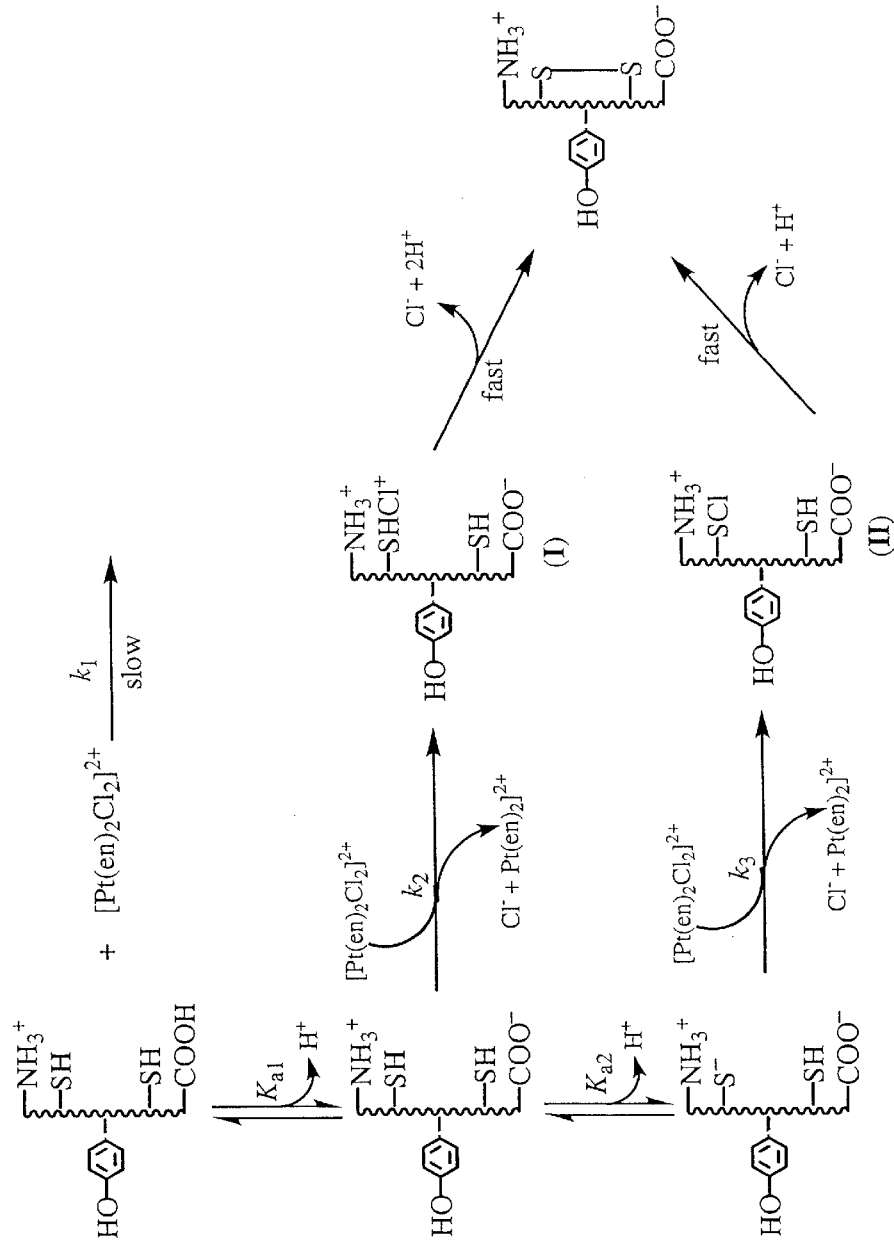
FIG. 7 shows scheme 1 illustrating a reaction mechanism for oxidation of peptide 8 by $[Pt(en)_2Cl_2]^{2+}$.

The rate law and k' vs pH de pendence for the reaction of [Pt(en)$_2$Cl$_2$]$^{2+}$ with 8 are similar to those found for reactions between trans-dichloro-platinum(IV) complexes and monothiols s uch as glutathione (Shi et al. (1996) *Inorg. Chem.* 35: 3498–3503). By analogy with the reaction mechanisms proposed previously for the oxidation of monothiols by Pt(IV) complexes (Id), a reaction mechanism for oxidation of peptide 8 by [Pt(en)$_2$Cl$_2$]$^{2+}$ is described in Scheme 1 (FIG. 7). The reaction proceeds through a transition state in which Cl$^+$ is transferred from the Pt(IV) center to an incoming thiol or thiolate nucleophile (Shi and Rabenstein (1999) *J. Org. Chem.* 64: 4590–4595; Shi et al. (1997) *J. Chem. Soc., Dalton Trans.* 2073–2077; Shi et al. (1996) *Inorg. Chem.* 35: 3498–3503; Shi and Elding (1998) *Inorg. Chim. Acta* 282: 55–60; Wilmarth et al. (1983) *Coord. Chem. Rev.* 51: 141–153). The mechanism in Scheme 1 shows all possible protonation states of 8 under the reaction conditions used in the kinetic study (Noszal et al. (1992) *J. Org. Chem.* 57: 2327–2334). However, as described above, there is little or no oxidation of peptide 8 by [Pt(en)$_2$Cl$_2$]$^{2+}$ in 1.00 M HCl, which indicates that oxidation of the fully protonated form of the peptide is negligibly slow. The reactions described by $k_2$ and $k_3$ are the rate-determining steps and are assumed to take place via parallel attack by thiol and thiolate on the coordinated chloride, resulting in a Cl$^+$ transfer from [Pt(en)$_2$Cl$_2$]$^{2+}$ to the attacking group (Shi and Rabenstein (1999) *J. Org. Chem.* 64: 4590–4595; Shi et al. (1997) *J. Chem. Soc., Dalton Trans.* 2073–2077; Shi et al. (1996) *Inorg. Chem.* 35: 3498–3503; Shi and Elding (1998) *Inorg. Chim. Acta* 282: 55–60; Wilmarth et al. (1983) *Coord. Chem. Rev.* 51: 141–153). The intermediates formed, denoted by I and II in Scheme 1, then undergo an intramolecular nucleophilic attack to form the disulfide bond. The rates of formation of the disulfide bond from intermediates I and II are expected to be largely controlled by conformational changes, which are expected to be fast relative to the atom transfer step (Creighton (1993) *Proteins: Structures and Molecular Properties*, 2nd Ed., Chapter 5, W.H. Freeman and Company: N.Y.). This is similar to what has been found in detailed studies of the kinetics of formation of intramolecular disulfide bonds in peptides such as 9–11 by thiol-disulfide exchange (Rabenstein and Yeo (1994) *J. Org. Chem.* 59: 4223–4229; Rabenstein and Weaver (1996) *J. Org. Chem.* 61: 7391–7397), where the nucleophilic displacement reaction in the second step of the overall intramolecular disulfide-bond forming reaction is formally similar to the nucleophilic displacement of Cl$^-$ from intermediates I and II. The relatively fast rates of ring closure by formation of intramolecular disulfide bonds by thiol-disulfide exchange reactions, even in the formation of the disulfide bond to give the 38-membered ring of somatostatin, are attributed to high effective concentrations of the attacking thiolate (Id).

The reaction rate increases almost exponentially as the solution pH is increased, which indicates that the thiolate anion is much more reactive than the protonated thiol forms.[23,24] Thus, at the pHs used in the kinetic studies, the reaction described by $k_3$ in Scheme 1 is the predominant oxidation pathway, while the reaction path described by $k_2$ contributes only slightly to the overall reaction at pH 3–5.

Reaction mechanisms similar to that described in Scheme 1 can be derived for the other peptides in Table 1. However, for peptide 14, reaction intermediates similar to I and II in Scheme 1 apparently undergo ring closure reactions more slowly due to steric hindrance from the two methyl groups on the deamino-penicillamine residue. Under such circumstances, the reaction intermediates are sufficiently long-lived that hydrolysis to form RSOH competes with ring closure by nucleophilic displacement of Cl⁻. The RSOH formed can then be further oxidized to give $RSO_2H$ and $RSO_3H$, or it can undergo intermolecular reactions with the thiol or thiolate groups of other molecules, resulting in formation of dimers and higher polymers.[6] This may explain the presence of up to ~3% side reaction products in the oxidation of peptide 14, as indicated by the extra peaks in the chromatograms shown in FIG. 4.

It also is of interest to compare the properties of $[Pt(en)_2Cl_2]^{2+}$ with those of $[Pt(CN)_4Cl_2]^{2-}$ as an oxidant for the formation of intramolecular disulfide bonds in peptides. $[Pt(CN)_4Cl_2]^{2-}$ is a somewhat stronger oxidizing agent, as indicated by its redox potential, and as a result it can rapidly convert dithiol peptides to their disulfide forms at lower pH (1–3) than $[Pt(en)_2Cl_2]^{2+}$. The disadvantage, however, is that $[Pt(CN)_4Cl_2]^{2-}$ is a sufficiently strong oxidizing agent that it can oxidize the sulfur of the methionine side chain. Similar reaction rates can be achieved with $[Pt(en)_2Cl_2]^{2+}$ by carrying out the reaction at higher pH (4–7) where a larger fraction is in the thiolate form, however oxidation of the methionine sulfur, which is a pH-independent oxidation, does not occur.

Conclusions.

We have discovered a highly selective and efficient reagent, trans-$[Pt(en)_2Cl_2]^{2+}$, for formation of intramolecular disulfide bonds in peptides. It rapidly and quantitatively converts the dicysteine peptide precursor, even at millimolar concentrations, to its disulfide form in slightly acidic and neutral media. As compared to $[Pt(CN)_4Cl_2]^{2-}$, $[Pt(en)_2Cl_2]^{2+}$ is a somewhat weaker oxidizing agent. No side reactions were observed with $[Pt(en)_2Cl_2]^{2+}$, including no oxidation of the methionine side chain. $[Pt(CN)_4Cl_2]^{2-}$ is a sufficiently strong oxidizing agent that it can rapidly oxidize dicysteine peptides at pH 1–3. Similar rates can be achieved with $[Pt(en)_2Cl_2]^{2+}$ by running the reaction at pH 4–7, where a larger fraction of the thiol groups are in the thiolate form. The Pt(IV) complex is also highly efficient for the oxidation of penicillamine-derived dithiol peptides. Moreover, $[Pt(en)_2Cl_2]^{2+}$ and its reduction product $[Pt(en)_2]^{2+}$ are essentially substitution inert under the conditions used for disulfide bond formation, nontoxic and readily separable from peptides by HPLC. Thus, $[Pt(en)_2Cl_2]^{2+}$ should be widely useful for the rapid and quantitative formation of intramolecular disulfide bonds in synthetic (or recombinantly expressed) peptides.

EXPERIMENTAL SECTION

Materials.

$[Pt(en)_2]Cl_2$ and dithiothreitol (DTT) were obtained from Aldrich. Phosphoric acid, sodium dihydrogen phosphate, sodium monohydrogen phosphate, trifluoroacetic acid (TFA) and HPLC-grade acetonitrile were purchased from Fisher Scientific Co. $[Pt(en)_2Cl_2]Cl_2$ was prepared from $[Pt(en)_2]Cl_2$ according to a literature method (Basolo et al. (1950) *J. Am. Chem. Soc.* 72: 2433–2438; Poë (1963) *J. Chem. Soc.* 183–188); the UV-visible spectrum was in good agreement with that reported. The peptide hormones pressinoic acid, oxytocin, arginine-vasopressin, and somatostatin, [Cys (Munson and Barany (1993) *J. Am. Chem. Soc.* 115: 10203–10216; Shi and Rabenstein (1999) *J. Org. Chem.* 64: 4590–4595), Tyr (Goldberg and Helper (1968) *Chem. Rev.* 68: 229–252), Pro (Shi et al. (1997) *J. Chem. Soc., Dalton Trans.* 2073–2077)]-Substance P (Lavielle et al. (1988) *J. Biochem. Pharmacol.* 37: 41–49) and [1-deaminopenicillamine, 2-(O-methyl)tyrosine]arginine-vasopressin (Bankowski, and Manning (1978) *Med. Chem.* 21: 850–853) were obtained from Bachem Inc. (Torrance, Calif.). The peptide ANF (11–30, frog) (Lazure et al. (1988) *FEBS Letters*, 238: 300–306) was supplied by PepSyn Co.

(Dublin, Calif.). Water was purified with a Millipore water purification system.

Peptide Synthesis and Purification.

Peptides 1–7 in Table 1 were synthesized on a Millipore Model 9050 Plus peptide synthesizer using FMOC solid phase peptide synthesis methods. A reagent of 88% TFA, 5% phenol, 5% water and 2% triisopropylsilane was used to cleave the peptide chain from the resin and remove side chain protecting groups; crude peptide product was obtained after lyophilization. Peptides 1–7 were isolated from the crude mixture by reversed-phase gradient HPLC on a 100 mm×250 mm C18 column with an acetonitrile-water mobile phase containing 0.1% TFA. The identities of the peptides were confirmed by molecular weight. Peptides 8–14 were prepared by reduction of their diisulfide forms with a large excess of DTT at pH 7.0 and were isolated from the reaction mixture using the same HPLC system.

Analysis of the Oxidation Reactions by HPLC.

Oxidation reaction mixtures were analyzed by isocratic HPLC on a 3.2 mm×100 mm C18 reversed-phase column (particle size 3 μm). The UV-detector was set at 215 nm. Mobile phases were prepared by addition of $NaH_2PO_4$ (0.10 M final concentration) and acetonitrile to water, and the pH was then adjusted to 2.5 with phosphoric acid. Chromatographic conditions were optimized for separation of the reduced dithiol and oxidized forms of the peptides by varying the percentage of acetonitrile in mobile phase.[33] HPLC mobile phases were filtered through a 0.45 μm cellulose nitrate filter, sparged with helium for ca. 15 min just before the experiment and were used for less than a week.

Conditions for Oxidation of Dicysteine Peptides with $[Pt(en)_2Cl_2]^{2+}$.

The optimum conditions for quantitative for mation of intramolecular peptide disulfide bonds are slightly acidic to neutral solution with a slight excess of $[Pt(en)_2Cl_2]^{2+}$. We have found it convenient to use a 2–10 mM stock solution of $[Pt(en)_2Cl_2]^{2+}$ in 1.00 M NaCl and phosphate buffer (pH 4–7) containing 1 mM EDTA. A solution of ca. 2 mM or less dithiol peptide (or crude peptide product cleaved from synthesis resin) is mixed with the $[Pt(en)_2Cl_2]^{2+}$ reagent in phosphate buffer, with $[Pt(en)_2Cl_2]^{2+}$ in slight excess. The mixture is allowed to react from 2 h (pH 4) to 30 min (pH 7), after which oxidation of the dithiol peptide to its disulfide form is complete.

Kinetic Measurements.

0.10 M phosphate buffer solutions at pH 3.0, 4.0, 5.0 and 6.0 which contained 1 mM EDTA were prepared. Stock solutions of ca. 1 mM peptide 8 were prepared by dissolving 8 in water and flushed with helium for 10 min. Each solution was only used for 1 h. Kinetic experiments were conducted by combining stock solutions of the reactants and buffer which were equilibrated at 25° C. before mixing. Ionic strength was adjusted to 0.45 M with stock solutions of 1.00 M NaCl. After initiation, the reaction mixture was kept at 25° C. throughout the experiment. Aliquots were removed as a function of time and quenched by adding an equal volume of 2.0 M HCl. The quenched solutions were then analyzed by isocratic HPLC within 4 h. Control experiments showed that the oxidation of 8 in 1.0 M HCl solution is negligibly slow, confirming that addition of the reaction mixture to 2.0 M HCl quenches the reaction.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of forming an intramolecular disulfide bond in a peptide, said method comprising:

contacting a peptide comprising at least two sulfhydryl (SH) groups with a compound having the formula:

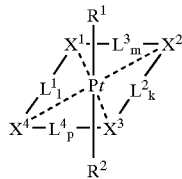

wherein $R^1$ and $R^2$ are independently selected from the group consisting of Cl—, Br—, I—, OH—, and $RCO_2$— where R is an alkyl or substituted alkyl;

Pt is Pt(IV);

$X^1$, $X^2$, $X^3$, and $X^4$ are ligands independently selected from the group consisting of a nitrogen ligand, an oxygen ligand, a phosphorous ligand, and a sulfur ligand;

i, k, m, and p are independently 0 or 1;

$L^1$, $L^2$, $L^3$, and $L^4$ when present, are independently selected linkers.

2. The method of claim 1, wherein said ligand is a nitrogen ligand selected from the group consisting of cyanide, ammonia, and an amine nitrogen.

3. The method of claim 1, wherein $X^1$, $X^2$, $X^3$, and $X^4$ are the same.

4. The method of claim 1, wherein $R^1$ and $R^2$ are the same.

5. The method of claim 1, wherein $L^1$ and $L^2$ are the same.

6. The method of claim 1, wherein i and k are 1 m and p are 0; and $L^1_i$ and $L^2_k$ are linkers selected from the group consisting of alkyl linkers, substituted alkyl linkers, and aromatic linkers.

7. The method of claim 6, wherein $L^1_i$ and $L^2_k$ are alkyl linkers comprising from 1 to 4 carbons.

8. The method of claim 7, wherein $R^1$ and $R^2$ are independently selected from the group consisting of Cl—, Br—, and I—.

9. The method of claim 7, wherein —$X^1$—$L^1$i—$X^4$— and —$X^2$—$L^2_k$—$X^3$— are both: —$NH_2CH_2CH_2NH_2$—.

10. The method of claim 1, wherein said peptide ranges in length from about 2 amino acids to about 60 amino acids.

11. The method of claim 1, wherein two amino acids that form a disulfide bond are adjacent amino acids.

12. The method of claim 1, wherein two amino acids that form a disulfide bond are separated by no more than about 58 amino acids.

13. The method of claim 9, wherein said peptide contains a methionine.

14. The method of claim 1, wherein said contacting is at a pH ranging from about pH 0 to about pH 9.

15. The method of claim 1, wherein said peptide is a chemically synthesized peptide.

16. The method of claim 1, wherein said peptide is a chemically synthesized peptide bearing a protecting group.

17. The method of claim 16, wherein said protecting group is an Fmoc or a tBoc.

18. The method of claim 1, wherein said peptide is attached to a substrate.

19. The method of claim 1, wherein $X^1$, $X^2$, $X^3$, and $X^4$ are not cyanide.

20. A solution comprising:

a peptide comprising at least two sulfhydryl groups; and a compound having the formula:

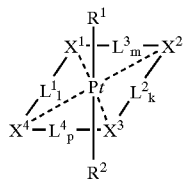

wherein $R^1$ and $R^2$ are independently selected from the group consisting of Cl—, Br—, I—, OH—, and $RCO_2$— where R is an alkyl or substituted alkyl;

Pt is Pt(IV);

$X^1$, $X^2$, $X^3$, and $X^4$ are ligands independently selected from the group consisting of a nitrogen ligand, an oxygen ligand, a phosphorous ligand, and a sulfur ligand;

i, k, m, and p are independently 0 or 1;

$L^1$, $L^2$, $L^3$, and $L^4$ when present, are independently selected linkers.

21. The solution of claim 20, wherein said ligand is a nitrogen ligand selected from the group consisting of cyanide, ammonia, and an amine nitrogen.

22. The solution of claim 20, wherein $X^1$, $X^2$, $X^3$, and $X^4$ are the same.

23. The solution of claim 20, wherein $R^1$ and $R^2$ are the same.

24. The solution of claim 20, wherein $L^1$ and $L^2$ are the same.

25. The solution of claim 20, wherein
i and k are 1;
m and p are zero; and
$L^1$ and $L^2$ are linkers selected from the group consisting of alkyl linkers, substituted alkyl linkers, and aromatic linkers.

26. The method of claim 25, wherein $L^1_i$ and $L^2_k$ are alkyl linkers comprising from 1 to 4 carbons.

27. The method of claim 26, wherein $R^1$ and $R^2$ are independently selected from the group consisting of Cl—, Br—, and I—.

28. The method of claim 26, wherein —$X^1$—$L^1_i$—$X^4$— and —$X^2$—$L^2_k$—$X^3$— are both:—$NH_2CH_2CH_2NH_2$—.

29. The solution of claim 25, wherein $L^1$ and $L^2$ are alkyl linkers comprising from 1 to 4 carbons.

30. The solution of claim 29, wherein $R^1$ and $R^2$ are the same and are selected from the group consisting of Cl—, Br—, and I—.

31. The solution of claim 29, wherein —$X^1$—$L^1$—$X^4$— and —$X^2$—$L^2$—$X^3$— are both:—$NH_2CH_2CH_2NH_2$—.

32. The solution of claim 20, wherein said peptide ranges in length from about 2 amino acids to about 100 amino acids.

33. The solution of claim 20, wherein two amino acids that form a disulfide bond are adjacent amino acids.

34. The solution of claim 20, wherein two amino acids that form a disulfide bond are separated by no more than 60 amino acids.

35. The solution of claim 20, wherein said peptide contains a methionine.

36. The solution of claim 20, wherein said solution has a pH ranging from about pH 1 to about pH 9.

37. The solution of claim 20, wherein said peptide is a chemically synthesized peptide.

38. The solution of claim 20, wherein said peptide is a chemically synthesized peptide bearing a protecting group.

39. The solution of claim 20, wherein said protecting group is an Fmoc or a tBoc.

40. The solution of claim 20, wherein said peptide is attached to a substrate.

41. A method of chemically synthesizing a peptide comprising a disulfide linkage, said method comprising:

chemically coupling a plurality of amino acids to form a peptide comprising at least two sulfhydryl (SH) groups; and contacting said peptide with a reagent having the formula:

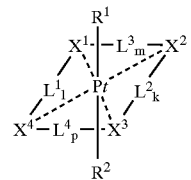

wherein $R^1$ and $R^2$ are independently selected from the group consisting of Cl—, Br—, I—, OH—, and $RCO_2$— where R is an alkyl of substituted alkyl;

Pt is Pt(IV);

$X^1$, $X^2$, $X^3$, and $X^4$ are ligands independently selected from the group consisting of a nitrogen ligand, an oxygen ligand, a phosphorous ligand, and a sulfur ligand;

i, k, m, and p are independently 0 or 1;

$L^1$, $L^2$, $L^3$, and $L^4$ when present, are independently selected linkers.

42. The method synthesizer of claim 41, wherein said ligand is a nitrogen ligand selected from the group consisting of cyanide, ammonia, and an amine nitrogen.

43. The method of claim 41, wherein said contacting is in a buffer having a pH ranging from about pH 1 to about pH 9.

44. A kit for forming an intramolecular disulfide bond in a peptide, said kit comprising:

a container containing a reagent having the formula:

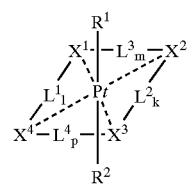

wherein $R^1$ and $R^2$ are independently selected from the group consisting of Cl—, Br—, I—, OH—, and $RCO_2$— where R is an alkyl or substituted alkyl;

Pt is Pt(IV);

$X^1$, $X^2$, $X^3$, and $X^4$ are ligands independently selected from the group consisting of a nitrogen ligand, an oxygen ligand, a phosphorous ligand, and a sulfur ligand;

i, k, m, and p are independently 0 or 1;

$L^1$, $L^2$, $L^3$, and $L^4$ when present, are independently selected linkers.

45. The kit of claim 43, wherein said ligand is a nitrogen ligand selected from the group consisting of cyanide, ammonia, and an amine nitrogen.

46. The kit of claim 43, wherein said reagent is in a buffer at a pH ranging from about pH 1 to about pH 9.

* * * * *

SEQUENCE LISTING

<160> NUMBER OF SEQ ID NOS: 14

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Cys Gly Pro Cys
1

<210> SEQ ID NO 2
<211> LENGTH: 4
<212> TYPE: PRT
<213> ORGANISM: Artificial Sequence
<220> FEATURE:
<223> OTHER INFORMATION: synthetic peptide

<400> SEQUENCE: 2

Cys Pro Phe Cys
1

<210> SEQ ID NO 3
<211> LENGTH: 6
<212> TYPE: PRT
<213> ORGANISM: Artificial Sequence
<220> FEATURE:
<223> OTHER INFORMATION: synthetic peptide

<400> SEQUENCE: 3

Thr Cys Pro Phe Cys Arg
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic peptide

<400> SEQUENCE: 4

Pro Thr Cys Pro Phe Cys Arg Lys
1               5

<210> SEQ ID NO 5
<211> LENGTH: 10
<212> TYPE: PRT
<213> ORGANISM: Artificial Sequence
<220> FEATURE:
<223> OTHER INFORMATION: synthetic peptide

<400> SEQUENCE: 5

Lys Pro Thr Cys Pro Phe Cys Arg Lys Thr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthetic peptide

<400> SEQUENCE: 6

```
Thr Asp Ile Thr Cys Gly Tyr Cys His Lys Leu His
1               5                   10
```

<210> SEQ ID NO 7
<211> LENGTH: 6
<212> TYPE: PRT
<213> ORGANISM: Artificial Sequence
<220> FEATURE:
<223> OTHER INFORMATION: synthetic peptide

<400> SEQUENCE: 7

```
Cys Tyr Phe Gln Asn Cys
1               5
```

<210> SEQ ID NO 8
<211> LENGTH: 6
<212> TYPE: PRT
<213> ORGANISM: Artificial Sequence
<220> FEATURE:
<223> OTHER INFORMATION: synthetic peptide

<400> SEQUENCE: 8

```
Cys Tyr Phe Gln Asn Cys
1               5
```

<210> SEQ ID NO 9
<211> LENGTH: 9
<212> TYPE: PRT
<213> ORGANISM: Artificial Sequence
<220> FEATURE:
<223> OTHER INFORMATION: synthetic peptide

<400> SEQUENCE: 9

```
Cys Tyr Ile Gln Asn Cys Pro Leu Gly
1               5
```

<210> SEQ ID NO 10
<211> LENGTH: 9
<212> TYPE: PRT
<213> ORGANISM: Artificial Sequence
<220> FEATURE:
<223> OTHER INFORMATION: synthetic peptide

<400> SEQUENCE: 10

```
Cys Tyr Phe Gln Asn Cys Pro Arg Gly
1               5
```

<210> SEQ ID NO 11
<211> LENGTH: 14
<212> TYPE: PRT
<213> ORGANISM: Artificial Sequence
<220> FEATURE:
<223> OTHER INFORMATION: synthetic peptide

<400> SEQUENCE: 11

```
Ala Gly Cys Lys Asn Phe Phe Trp Lys Thr Phe Thr Ser Cys
1               5                   10
```

<210> SEQ ID NO 12
<211> LENGTH: 11
<212> TYPE: PRT
<213> ORGANISM: Artificial Sequence
<220> FEATURE:
<223> OTHER INFORMATION: synthetic peptide

<400> SEQUENCE: 12

```
Arg Pro Cys Pro Gln Cys Phe Tyr Pro Leu Met
```

```
                1               5                    10

<210> SEQ ID NO 13
<211> LENGTH: 20
<212> TYPE: PRT
<213> ORGANISM: Artificial Sequence
<220> FEATURE:
<223> OTHER INFORMATION: synthetic peptide

<400> SEQUENCE: 13

Cys Phe Gly Ser Arg Ile Asp Arg Ile Gly Ala Gln Ser Gly Met Gly
1               5                   10                  15

Cys Gly Arg Phe
            20

<210> SEQ ID NO 14
<211> LENGTH: 7
<212> TYPE: PRT
<213> ORGANISM: Artificial Sequence
<220> FEATURE:
<223> OTHER INFORMATION: synthetic peptide

<400> SEQUENCE: 14

Phe Gln Asn Cys Pro Arg Gly
1               5
```